United States Patent [19]

Judd et al.

[11] 4,288,443
[45] Sep. 8, 1981

[54] SUBSTITUTED FURAN COMPOUNDS AND PHARMACEUTICAL COMPOSITIONS CONTAINING THEM

[75] Inventors: Duncan B. Judd, Ware; John W. Clitherow, Sawbridgeworth; Barry J. Price, Hertford; John Bradshaw, Ware, all of England

[73] Assignee: Glaxo Group Limited, London, England

[21] Appl. No.: 124,115

[22] Filed: Feb. 25, 1980

Related U.S. Application Data

[63] Continuation of Ser. No. 950,440, Oct. 11, 1978, abandoned.

[30] Foreign Application Priority Data

Oct. 11, 1977 [GB] United Kingdom ............... 42256/77

[51] Int. Cl.$^3$ ..................... A61K 31/34; C07D 307/54
[52] U.S. Cl. ............................... 424/267; 260/326.36; 260/326.5 S; 260/326.5 SF; 260/326.5 D; 260/347.2; 260/347.3; 260/347.5; 260/347.7; 424/274; 424/248.5; 424/248.52; 424/248.54; 424/248.56; 424/250; 424/251; 424/272; 424/273 R; 424/285; 544/63; 544/96; 544/152; 544/238; 544/333; 544/379; 546/214; 548/215; 548/240; 548/300; 548/356
[58] Field of Search ........... 260/347.2, 347.7, 326.5 S, 260/347.3, 347.5, 326.36, 326.5 D, 326.5 SF; 424/274, 248.5, 285, 248.52, 248.54, 248.56, 250, 251, 267, 273 R, 272; 544/63, 96, 152, 238, 333, 379; 546/214; 548/215, 240, 300, 356

[56] References Cited

U.S. PATENT DOCUMENTS 4,128,658 12/1978 Price et al. .......................... 424/285

*Primary Examiner*—Richard Raymond
*Attorney, Agent, or Firm*—Bacon & Thomas

[57] ABSTRACT

The invention relates to compounds of the general formula

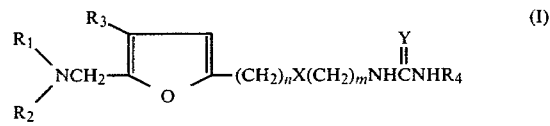
(I)

and physiologically acceptable salts and N-oxides, hydrates and bioprecursors thereof, in which $R_1$ and $R_2$ which may be the same or different each represent hydrogen, $C_{1-8}$ alkyl, $C_{4-8}$ cycloalkyl, $C_{3-6}$ alkenyl, aralkyl with 1 to 4 carbon atoms in the alkyl residue or $C_{1-8}$ alkyl interrupted by an oxygen atom or a group

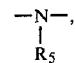

in which $R_5$ represents hydrogen or $C_{1-8}$ alkyl, or $R_1$ and $R_2$ may together with the nitrogen atom to which they are attached, form a saturated monocyclic 5 to 7 membered heterocyclic ring which may additionally contain the heterofunction O or

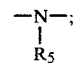

$R_3$ represents straight or branched chain $C_{1-8}$ alkyl, alkoxyalkyl with 1 to 8 carbon atoms in each alkyl residue, $C_{1-8}$ hydroxyalkyl, $C_{1-8}$ alkoxycarbonyl, alkyl thioalkyl with 1 to 8 carbon atoms in each alkyl residue, halogen or aryl;

$R_4$ represents hydrogen, $C_{1-8}$ alkyl, $C_{3-6}$ alkenyl or alkoxyalkyl with 1 to 8 carbon atoms in each alkyl residue;

X represents —O— or —S—;

Y represents =S, =O, =NR$_6$ or =CHNO$_2$ where $R_6$ represents hydrogen, nitro, cyano, $C_{1-8}$ alkyl, aryl, $C_{1-8}$ alkylsulphonyl or arylsulphonyl;

m represents an integer from 2 to 4 inclusive; and n represents an integer which is 1 or 2, or additionally when X is —S— n may also be zero.

The invention also relates to processes for the production of such compounds, pharmaceutical compositions containing them and certain novel intermediates used in their production, i.e. amines of the formula

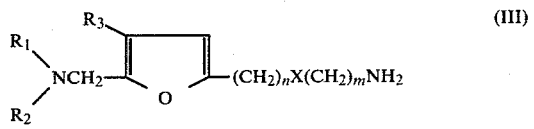
(III)

and alcohols of the formula

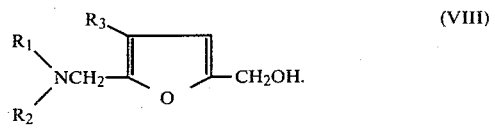
(VIII)

The compounds of formula (I) show pharmacological activity as selective histamine $H_2$-antagonists.

6 Claims, No Drawings

SUBSTITUTED FURAN COMPOUNDS AND PHARMACEUTICAL COMPOSITIONS CONTAINING THEM

This is a continuation, of application Ser. No. 950,440, filed Oct. 11, 1978, now abandoned.

This invention relates to new substituted heterocyclic compounds having a selective action on histamine receptors, to processes for the preparation thereof and to pharmaceutical compositions containing them, as well as to their use in therapeutics.

We have found that certain novel aminoalkyl furan derivatives are selective $H_2$-antagonists, that is they show inhibition of the secretion of gastric acid when this is stimulated via histamine $H_2$-receptors (Ash and Schild Brit. J. Pharmacol, Chemother, 1966, 27 427). Their ability to do so can be demonstrated in the perfused rat stomach, using the preparation described in German Offenlegungsschrift No. 2,734,070. The compounds also antagonise the effect of histamine on the contraction frequency of isolated guinea pig right atrium. The compounds according to the invention do not modify histamine induced contractions of isolated gastrointestinal smooth muscle.

Compounds with histamine $H_2$-blocking activity may be used in the treatment of conditions where there is a hypersecretion of gastric acid e.g. in gastric and peptic ulceration, as a prophylactic measure in surgical procedures, and in the treatment of allergic conditions where histamine is a known mediator. Thus they may be used, either alone, or in combination with other active ingredients in the treatment of allergic and inflammatory conditions such as urticaria.

The invention therefore provides compounds of general formula (I):

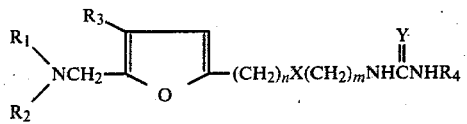

and physiologically acceptable salts and N-oxides, hydrates and bioprecursors thereof, in which $R_1$ and $R_2$ which may be the same or different each represent hydrogen, $C_{1-8}$ alkyl, $C_{4-8}$ cycloalkyl, $C_{3-6}$ alkenyl, aralkyl with 1 to 4 carbon atoms in the alkyl residue or $C_{1-8}$ alkyl interrupted by an oxygen atom or a group

in which $R_5$ represents hydrogen or $C_{1-8}$ alkyl, or $R_1$ and $R_2$ may together with the nitrogen atom to which they are attached, form a saturated monocyclic 5 to 7 membered heterocyclic ring which may additionally contain the heterofunction —O— or

$R_3$ represents straight or branched chain $C_{1-8}$ alkyl, alkoxyalkyl with 1 to 8 carbon atoms in each alkyl residue, $C_{1-8}$ hydroxyalkyl, $C_{1-8}$ alkoxycarbonyl, alkyl thioalkyl with 1 to 8 carbon atoms in each alkyl residue, halogen or aryl;

$R_4$ represents hydrogen, $C_{1-8}$ alkyl, $C_{3-6}$ alkenyl or alkoxyalkyl with 1 to 8 carbon atoms in each alkyl residue;

X represents —O— or —S—;

Y represents =S, =O, =NR$_6$ or =CHNO$_2$ where R$_6$ represents hydrogen, nitro, cyano, $C_{1-8}$ alkyl aryl, $C_{1-8}$ alkylsulphonyl or arylsulphonyl;

m represents an integer from 2 to 4 inclusive; and n represents an integer which is 1 or 2, or additionally when X is —S— n may also be zero.

The compounds according to the invention are particularly preferred in the form of the free bases and their physiologically acceptable salts.

The cycloalkyl group preferably has 5 or 6 carbon atoms. The term 'aryl' when applied to aryl groups or the aryl portion of groups means preferably phenyl or substituted phenyl e.g. by one or more $C_{1-4}$ alkyl, $C_{1-4}$ alkoxy or halogen groups. The aralkyl groups preferably have 1 or 2 carbon atoms in the alkyl residue.

The compounds of formula I can exhibit tautomerism and the invention extends to all tautomers.

A preferred class of compounds of formula I is that defined by the following formula (II):

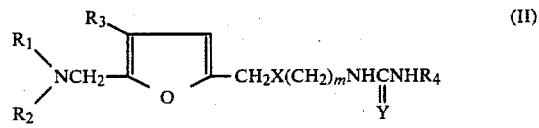

and their physiologically acceptable salts, in which $R_1$ represents hydrogen or $C_{1-4}$ alkyl and $R_2$ represents $C_{1-4}$ alkyl or $R_1$ and $R_2$ together with the nitrogen atom form a pyrrolidine ring;

$R_3$ represents straight or branched chain $C_{1-4}$ alkyl, alkoxymethyl with 1 to 4 carbon atoms in the alkyl residue, hydroxymethyl, alkoxycarbonyl with 1 to 4 carbon atoms in the alkyl residue, phenyl or bromine;

X represents —S— or —O;

Y represents =S, =NR$_6$ or =CHNO$_2$ in which R$_6$ represents nitro, cyano or $C_{1-4}$ alkylsulphonyl;

$R_4$ represents hydrogen or $C_{1-4}$ alkyl; and m represents an integer which is 2 or 3.

Particularly preferred compounds are: N-[2-[[5-(dimethylaminomethyl)-4-methyl-2-furanylmethyl]thio]ethyl]-N'-methyl-2-nitro-1,1-ethenediamine; N"-cyano-N-[2-[[5-(dimethylaminomethyl)-4-methyl-2-furanylmethyl]thio]ethyl]-N'-methylguanidine; N-[2-[[5-(dimethylaminomethyl)-4-methyl-2-furanylmethyl]thio]ethyl]-N'-nitroguanidine; N-[2-[[5-(dimethylaminomethyl)-4-methyl-2-furanylmethyl]thio]ethyl]-N"-methanesulphonyl-N'-methylguanidine; N-methyl-N'-[2-[[4-methyl-5-(1-pyrrolidinylmethyl)-2-furanylmethyl]thio]ethyl]-2-nitro-1,1-ethenediamine; N-methyl-N'-[2-[[4-methyl-5-(methylaminomethyl)-2-furanylmethyl]thio]ethyl]-2-nitro-1,1-ethenediamine; N-[2-[[5-(dimethylaminomethyl)-4-(1-methylethyl)-2-furanylmethyl]thio]ethyl]-N'-methyl-2-nitro-1,1-ethenediamine; 2-(dimethylaminomethyl)-5-[[2-[[1-(methylamino)-2-nitroethenyl]amino]ethyl]thio]methyl-3-furanmethanol; N'-[2-[[4-bromo-5-(dimethylaminomethyl)-2-furanylmethyl]thio]ethyl]-N'-methyl-2-nitro-1,1-ethenediamine; N-[2-[[5-(dimethylaminomethyl)-4-methoxymethyl-2-furanylmethyl]thio]ethyl]-N'-methyl-2-nitro-1,1-ethenediamine and N-[3-[5-(dimethylaminomethyl)-4-methyl-2-furanylmethoxy]propyl]-

N'-methyl-2-nitro-1,1-ethenediamine and their physiologically acceptable salts.

The invention includes the compounds of formula (I) in the form of physiologically acceptable salts with inorganic and organic acids. Particularly useful salts include hydrochloride, hydrobromides and sulphates; acetates, maleates and fumarates. The compounds and their salts may also form hydrates.

The compounds may be used in the treatment of conditions where there is a hypersecretion of gastric acid e.g. in gastric and peptic ulceration, as a prophylactic measure in surgical procedures, and in the treatment of allergic conditions where histamine is a known mediator.

The compounds according to the invention may be formulated for administration in any convenient way and the invention includes within its scope pharmaceutical compositions containing at least one compound according to the invention adapted for use in human or veterinary medicine. Such compositions may be formulated in conventional manner using one or more pharmaceutically acceptable carriers or excipients. Such compositions may also contain other active ingredients, e.g. conventional anti-histamines if required.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays. Ointments and creams may, for example, be formulated with an aqueous or oily base with the addition of suitable pharmaceutical excipients. Lotions may be formulated with an aqueous or oily base and will include the necessary adjustments to ensure pharmaceutically acceptable products. Spray compositions may, for example, be formulated as aerosols which may be pressurised by means of a suitable dichlorofluoromethane or trichlorofluoromethane or may be delivered by means of a hand-operated atomizer.

A convenient daily dose by the oral route would be of the order of 50 mg to 1.2 g per day, preferably 100 to 500 mg per day, in the form of dosage units containing from 10 to 200 mg per dosage unit. Solutions for injection may contain from 10 to 100 mg/ml of the compound.

The compounds of the present invention may be prepared by reacting a primary amine of the formula (III):

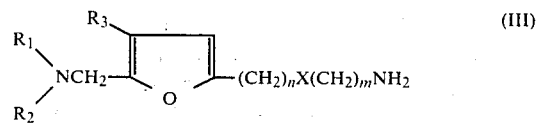

in which $R_1$, $R_2$, $R_3$, n, X and m are as defined in formula (I) with a compound capable of converting the group $NH_2$ into a group

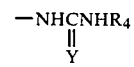

in which $R_4$ and Y are as defined in formula (I). Compounds which are capable of effecting this conversion are, isocyanates $R_4NCO$, isothiocyanates $R_4NCS$, or compounds of the formula (IV):

where Q represents a group $=NR_6$ or $=CHNO_2$ and P is a leaving group such as halogen, thiomethyl, 3,5-dimethylpyrazolyl or alkoxy, preferably thiomethyl or chlorine.

The reaction with the isocyanate or isothiocyanate may be carried out in a suitable solvent such as acetonitrile or an alkanol, e.g. ethanol. To prepare compounds of formula (I) where $R_4$ represents hydrogen, alkali metal cyanates and thiocyanates may be used. Alternatively, organic isocyanates or isothiocyanates may be used, e.g. ethylcarbonisothiocyanatidate, followed by basic hydrolysis.

The reaction of the amine (III) with the compound of formula (IV) can be carried out by heating the reactants directly at for example 100°-120° C. or in a solvent such as acetonitrile or an alkanol, e.g. ethanol at ambient to reflux temperature. Where Q is $=CHNO_2$, the amine (III) and the compound (IV) may alternatively be reacted in aqueous solution.

The introduction of the group

where Y is $=NR_6$ or $=CHNO_2$ and where $R_6$ is as defined in formula (I) except that it is other than $-NO_2$, may also be effected by first reacting the amine (III) with a compound of the formula:

in which P is as defined in formula (IV), Q is $=NR_6$ or $=CHNO_2$ where $R_6$ is as defined in formula (I) except that $R_6$ is other than $NO_2$ and $P^1$ may have the same meanings as P or may be a group

wherein A represents a $C_{1-4}$ alkyl group e.g. methyl, in a non hydroxylic solvent e.g. ethyl acetate, dimethyl formamide or dioxan. The resulting compound of formula (VI):

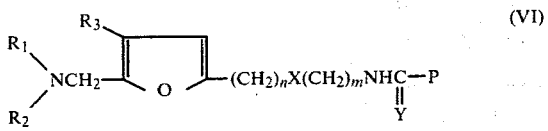

may then be reacted with a primary amine $R_4NH_2$ in a suitable solvent, e.g. water or an alkanol, e.g. ethanol, at a temperature from ambient to reflux, to give a compound of formula (I).

In an alternative procedure for the production of products in which Y is sulphur and $R_1$ and $R_2$ are other than hydrogen, the amine (III) in which $R_1$ and $R_2$ are other than hydrogen can be heated with carbon disulphide and then reacted with a chloroformate ester, e.g. ethyl chloroformate to form an isothiocyanate (VII) which is then reacted with an amine $R_4NH_2$, preferably in an inert solvent such as acetonitrile, tetrahydrofuran or dioxan.

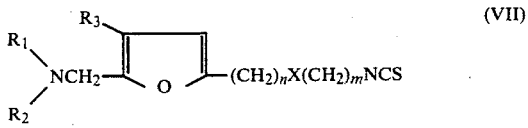

To prepare compounds by this process where $R_1$ and $R_2$ are both hydrogen it is possible to protect the group $-NR_1R_2$ as a phthalimido group. The primary amine will be regenerated during reaction with the amine $R_4NH_2$.

In another process, compounds wherein X is sulphur and n is 1, (and then $R_1$ and $R_2$ are both hydrogen, Y is other than $=CHNO_2$) can be prepared from starting materials of formulae (VIII) or (IX):

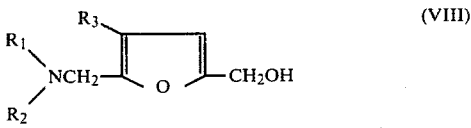

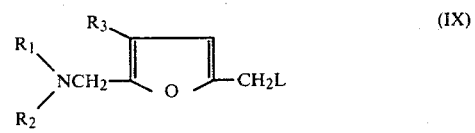

in which $R_1$, $R_2$ and $R_3$ are as defined in formula (I) and l is a leaving group such as halogen, e.g. chlorine, or acyloxy, e.g. acetoxy. Where products in which $R_1$ and $R_2$ are hydrogen are desired, the primary amino group $(NR_1R_2=NH_2)$ is protected in compounds of formulae (VIII) and (IX) as, for example, a phthalimido group. The above compounds may be reacted with a thiol of the formula (X)

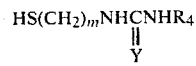

in which Y, $R_4$ and m are as defined in formula (I) except that when $R_1$ and $R_2$ are both hydrogen, Y is other than $=CHNO_2$, with subsequent deprotection if necessary at a suitable stage by conventional means e.g. cleavage of a phthalimido group using a primary amine or a hydrazine, for example, methylamine or hydrazine hydrate. When a compound of formula (VIII) is used the reaction is preferably carried out at $-10°$ C. to $+10°$ C., preferably $0°$ C., in a mineral acid e.g. concentrated hydrochloric acid. When a compound of formula (IX) is used the reaction may be carried out in the presence of a strong base, e.g. sodium hydride in dimethyl formamide or a sodium alkoxide in the corresponding alkanol, at $0°$ to $20°$ C. The starting materials of formula (IX) may be prepared from the corresponding alcohols of formula (VIII) by conventional means.

For the preparation of compounds in which $R_1$ and $R_2$ are hydrogen it is frequently convenient to carry out reactions with starting materials in which the primary amino group is protected, for example as a phthalimido group, which protecting group can be cleaved by conventional means at a suitable stage.

The free bases of formula (I) may be converted into salts by standard procedures, for example by reaction with the appropriate acid.

In the above discussion of the processes available for the production of the compounds according to the invention reference has been made to primary amines of formula (III). These amines are novel compounds and the invention includes such compounds. These intermediates may be made by a number of processes which are described below.

Amines of formula (III) wherein n is 1 may be prepared by reacting a compound of formula (VIII) with an $\omega$-aminoalkylthiol or an $\omega$-aminoalkanol, in which the amine group may be protected if desired, under acid conditions, for example in the presence of hydrogen chloride or methane sulphonic acid in a suitable solvent, for example water or tetrahydrofuran. Alternatively, a compound of formula (IX) may be treated under basic conditions with the $\omega$-aminoalkyl thiol to give amines of formula (III) wherein X is sulphur and n is 1.

To prepare amines of formula (III) in which $R_1$ and $R_2$ are other than hydrogen, $R_3$ is other than hydroxyalkyl or alkoxycarbonyl, n is zero and X is sulphur, a compound of formula (XI)

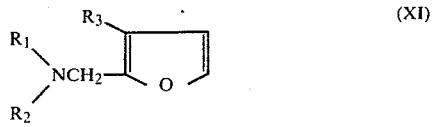

may be treated with lithium and elemental sulphur followed by reaction with an $\omega$-bromoalkylphthalimide (XII):

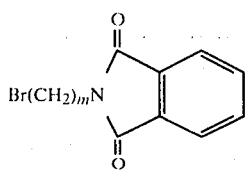
(XII)

The phthalimido protecting group in the resulting product of formula (XIII)

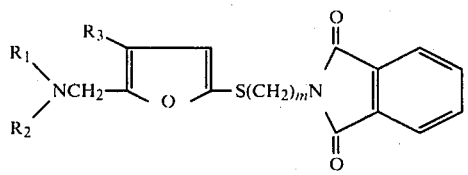
(XIII)

may be cleaved by means described above.

An amine of formula (III) wherein X is an oxygen atom and n is 1 may be obtained by treating a compound of formula (VIII) with a compound Hal $(CH_2)_mNH_2$ where Hal represents a halogen atom, preferably chlorine, in the presence of a base, particularly potassium tertiary butoxide, in a suitable solvent such as dimethylformamide.

Amines of formula (III) in which $R_3$ is hydroxymethyl can be prepared from the corresponding compounds in which $R_3$ is alkoxycarbonyl by reduction for example with aluminium hydride in tetrahydrofuran.

Amines of formula (III) wherein X is sulphur and n is 1 and $R_1$ and/or $R_2$ is hydrogen may be prepared by reduction of the amide function in a compound of formula (XIV)

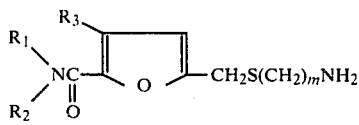
(XIV)

using, for example, aluminium hydride.

The compounds of formula (XIV) may be prepared by treatment of a compound of formula (XV)

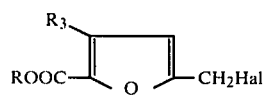
(XV)

in which Hal represents a halogen atom, preferably chlorine and R is an alkyl group e.g. methyl, with an ω-phthalimidoalkylthiol of formula (XVI)

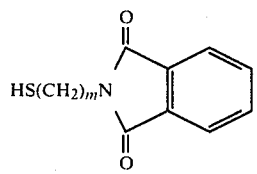
(XVI)

in which m is as defined in formula (I).

The product of this reaction may then be reacted by conventional means to give a compound of formula (XIV), e.g. with a primary amine $R_1R_2NH$ in the presence of a base e.g. sodium methoxide.

Where $R_1$ and $R_2$ are both hydrogen, they may be protected, if desired, in any of the reaction stages, as a phthalimido group. The protecting group may be cleaved, at any suitable stage in the reaction using methods described herein.

The alcohols of formula (VIII) are also novel compounds and the invention includes such compounds. These alcohols may be prepared by a number of processes which are described below.

Alcohols of formula (VIII) in which $R_3$ is alkyl, alkoxyalkyl, aryl or alkylthioalkyl and $R_1$ and $R_2$ are other than hydrogen may be made by reacting an ester of formula (XVII)

(XVII)

where COOR is an esterified carboxyl group, e.g. the methyl ester, with an amine of formula $R_1R_2NH$ in the presence of a base, for example sodium methoxide to produce a compound of formula (XVIII)

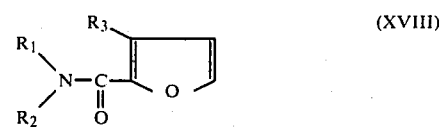
(XVIII)

The compound of formula (XVIII) is reduced for example with lithium aluminium hydride to produce a compound of formula (XI) which is reacted to form the alcohol of formula (VIII), for example when $R_3$ is alkyl with butyl lithium and paraformaldehyde or when $R_3$ is alkoxyalkyl with paraformaldehyde acetic acid and hydrogen chloride.

Alcohols of formula (VIII) in which $R_3$ is alkoxy carbonyl and $R_1$ and $R_2$ are both methyl may be prepared by reducing an aldehyde of formula (XIX)

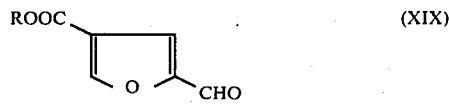
(XIX)

in which COOR is an esterified carboxyl group, e.g. the ethyl ester, with for example sodium borohydride to an alcohol of formula (XX)

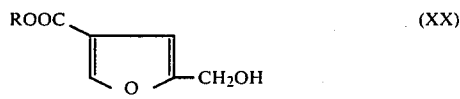
(XX)

The alcohol is reacted with the reagent $(CH_3)_2N^{\oplus}=CH_2\ Cl^{\ominus}$ to produce an alcohol of formula (XXI)

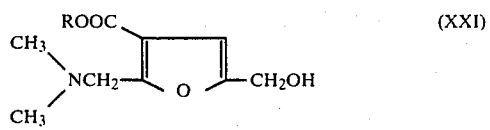
(XXI)

The reagent $(CH_3)_2N^{\oplus}=CH_2\ Cl^{\ominus}$ can also be used to make alcohols of formula (VIII) in which $R_1$ and $R_2$ are both methyl and $R_3$ is halogen by reacting it with an alcohol of formula (XXII)

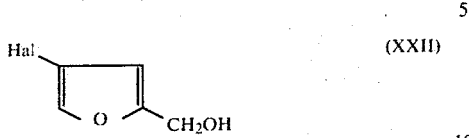
(XXII)

Alcohols of formula (VIII) in which $R_1$ and $R_2$ are other than methyl may be prepared from alcohols in which $R_1$ and $R_2$ are both methyl by quaternisation of the amino group followed by displacement with the appropriate amine $R_1R_2NH$.

The invention is illustrated by the following Examples.

PREPARATION 1

(a)
N,N-Dimethyl-3-(1-methylethyl)-2-furancarboxamide

A solution of sodium methoxide (3.3 g) and 3-(1-methylethyl)-2-furancarboxylic acid, methyl ester (14 g) in dry methanol (50 ml) was treated with dimethylamine gas during 2 hours. The solvent was removed in vacuo and the residue was dissolved in diethyl ether (150 ml) and washed with water (100 ml). The ethereal extract was dried over anhydrous sodium sulphate and evaporation of the solvent gave the title compound (12 g) as an oil.

UV λ max (ethanol) 227 nm (sh); 253 nm (ε 7,200, 9,250). GLC 15% E.G.S. at 160° retention time 6.8 min.

Similarly prepared from the corresponding esters were:

(b) 1-(3-Methyl-2-furanylcarbonyl)pyrrolidine (23 g) from ester (19.5 g)

Found: C, 66.9; H, 7.3; N, 7.9; $C_{10}H_{13}NO_2$ requires: C, 67.0; H, 7.3; N, 7.8%.

UV λ max (ethanol) 256 nm (ε 12,400).

(c)
3-Methoxymethyl-N,N-dimethyl-2-furancarboxamide (3 g) from ester (3.7 g)

Found: C, 59.1; H, 7.1; N, 7.8; $C_9H_{13}NO_3$ requires: C, 59.0; H, 7.2; N, 7.7%.

UV λ max (ethanol) 254 nm (ε 9,050).

PREPARATION 2

(a)
N,N-Dimethyl-3-(1-methylethyl)-2-furanmethanamine

A solution of N,N-dimethyl-3-(1-methylethyl)-2-furanecarboxamide (12 g) in dry tetrahydrofuran (250 ml) was treated with lithium aluminium hydride (4.2 g). After 1 hour water (6 ml) was added and the filtered solution evaporated in vacuo. The residue was dissolved in 1 M hydrochloric acid (100 ml) and the solution was washed with diethyl ether (100 ml). The aqueous phase was basified and extracted with diethyl ether (2 × 150 ml), which was dried over anhydrous sodium sulphate. The solvent was removed in vacuo to yield the title compound (7 g) as an oil.

The picrate salt was formed in and recrystallised from ethanol, m.p. 111°.

Found: C, 48.4; H, 5.0; N, 14.3; $C_{10}H_{17}NO.C_6H_3N_3O_7$ requires: C, 48.5; H, 5.1; N, 14.1%.

Similarly prepared from the corresponding carboxamides were:

(b) 1-(3-Methyl-2-furanylmethyl)pyrrolidine (15 g) from carboxamide (17 g)

Picrate salt, m.p. 113°.

Found: C, 58.7; H, 4.6; N, 14.1; $C_{10}H_{15}NO.C_6H_3N_3O_7$ requires: C, 48.7; H, 4.6; N, 14.2%.

(c)
3-Methoxymethyl-N,N-dimethyl-2-furanmethanamine (1 g) from carboxamide (1.5 g)

Picrate salt, m.p. 73°–74°.

Found: C, 45.3; H, 4.6; N, 14.1; $C_9H_{15}NO_2.C_6H_3N_3O_7$ requires: C, 45.2; H, 4.6; N, 14.1%.

PREPARATION 3

(a)
4-Bromo-5-(dimethylaminomethyl)-2-furanmethanol, hydrochloride

A mixture of 4-bromo-2-furanmethanol (3.6 g) and dimethyl (methylene) ammonium chloride (3.0 g) in dry acetonitrile was stirred at ambient temperature for 18 hours. The resulting precipitate was crystallised from acetonitrile affording the title compound (3.0 g) m.p. 190° dec.

Found: C, 35.5; H, 4.9; N, 5.1; $C_8H_{12}BrNO_2.HCl$ requires: C, 35.5; H, 4.8; N, 5.2%.

Similarly prepared from the corresponding furanmethanol (14 g) was:

(b)
2-(Dimethylaminomethyl)-5-hydroxymethyl-3-furancarboxylic acid, ethyl ester (18 g)

Oxalate salt, m.p. 97°–99°.

Found: C, 49.0; H, 6.0; N, 4.4; $C_{11}H_{17}NO_4$ requires: C, 49.2; H, 6.0; N, 4.4%.

PREPARATION 4

5-(Dimethylaminomethyl)-4-methoxymethyl-2-furanmethanol

A mixture of 3-methoxymethyl-N,N-dimethyl-2-furanmethanamine (7 g), acetic acid (60 ml), concentrated hydrochloric acid (30 ml) and paraformaldehyde (3.7 g) was stirred at ambient temperature for 5 hours. The mixture was basified with sodium carbonate, and extracted with diethyl ether (200 ml). The ethereal extract was dried over anhydrous sodium sulphate and the solvent evaporated in vacuo. The residue was distilled affording the title compound (3.5 g) as an off-white waxy solid, b.p. 90°/5×10$^{-2}$ mm Hg.

The oxalate salt was formed in and recrystallised from ethanol/ethyl acetate m.p. 102°–4°.

Found: C, 49.7; H, 6.8; N, 4.8; $C_{10}H_{17}NO_3.H_2C_2O_4$ requires: C, 49.8; H, 6.6; N, 4.8%.

PREPARATION 5

(a) 5-(Dimethylaminomethyl)-4-methyl-2-furanmethanol

A solution of N,N,3-trimethyl-2-furanmethanamine (10.3 g) in dry tetrahydrofuran (200 ml) under nitrogen was treated over 2 hr with 1.6 M n-butyl lithium in hexane 846.2 ml) at −40° to −45° C. After stirring for 2 hr at room temperature paraformaldehyde (2.3 g) in dry tetrahydrofuran (100 ml) was added and the solution stirred overnight. Water (10 ml) was added and the solvent evaporated. Ethyl acetate (200 ml) and sodium sulphate were added and the organic phase was evaporated giving an oily residue which was distilled (85°/0.1 mm) affording the title compound (8 g).

The oxalate salt was formed and recrystallised from ethanol, m.p. 104°–106°.

Found: C,49.1; H,6.7; N,5.1; $C_9H_{15}NO_2.H_2C_2O_4.\frac{1}{2}H_2O$ requires: C,49.3; H,6.8; N,5.2%.

Similarly prepared from the corresponding furanmethanamines were:

(b) 4-Methyl-5-(1-pyrrolidinylmethyl)-2-furanmethanol (7.5 g) from the furanmethanamine (12 g) m.p. 86°–88°

Found: C,67.3; H,9.0; N,7.2; $C_{11}H_{17}NO_2$ requires: C,67.7; H,8.8; N,7.2%.

(e)
5-(Dimethylaminomethyl)-4-(1-methylethyl)-2-furanmethanol (8 g)

From the furanmethanamine (6.8 g) m.p. oxalate salt 122°–124°.

Found: C,54.4; H,7.5; N,4.9; $C_{11}H_{19}NO_2.H_2C_2O_4$ requires: C,54.3; H,7.4; N,4.9%.

EXAMPLE A (a) 5-[[-(Amino)ethyl]thio]methyl-N,N,3-trimethyl]furanmethanamine

A stirred solution of 2-aminoethanethiol hydrochloride (4.65 g) in concentrated hydrochloric acid (20 ml) was treated with 5-(dimethylaminomethyl)-4-methyl-2-furanmethanol (7 g). The mixture was stirred at 0° C. for 1 hr and kept at 0° overnight. Ethyl acetate (200 ml) and anhydrous sodium carbonate were added, and the friable solid was collected by filtration. The filtrate was evaporated in vacuo and the oily residue which resulted was distilled (100°/0.1 mm) to give the title compound (6.7 g). The oxalate salt was formed in and recrystallised from ethanol m.p. 175° dec.

Found: C,43.7; H,6.0; N,6.9; $C_{11}H_{20}N_2OS.2H_2C_2O_4$ requires: C,44.1; H,5.9; N,6.9%. Similarly prepared from 2-aminoethanethiol hydrochloride (A) and the corresponding funanmethanol were:

(b)
5-[[2-(Amino)ethyl]thio]methyl-N,N-dimethyl-3-(1-methylethyl)-2-furanmethanamine (6.5 g) from the furanmethanol (7 g) and A (4 g)

B.p. 125°/$10^{-1}$ mm Hg, oxalate salt m.p. 186° dec.
Found: C,46.4; H,6.7; N,6.4; $C_{13}H_{24}N_2OS.2H_2C_2O_4$ requires: C,46.8; H,6.5; N,6.4%.

(c)
5-[[2-(Amino)ethyl]ethyl]thio]methyl-2-(dimethylaminomethyl)-3-furancarboxylic acid, ethyl ester, hydrate (1.5 g) from the furanmethanol (5 g) and A (2.5 g)

IR (CHBr$_3$) C=O 1708 cm$^{-1}$.
Found: C,51.7; H,7.7; N,9.2; $C_{13}H_{22}N_2O_3S.H_2O$ requires: C,51.3; H,7.9; N,9.2%.

(d)
5-[[2-(Amino)ethyl]thio]methyl-3-bromo-N,N-dimethyl-2-furanmethanamine (1.2 g) from the furanmethanol (2.7 g) and A (1.1 g)

B.p. 120°/$2\times10^{-2}$ mm Hg, oxalate salt m.p. 70°–72°.
Found: C,33.9; H,4.3; N,5.2; $C_{10}H_{17}BrN_2OS.2H_2C_2O_4.H_2O$ requires: C,34.2; H,4.7; N,5.7%.

(e)
5-[[2-(Amino)ethyl]thio]methyl-3-methoxymethyl-N,N-dimethyl-2-furanmethanamine (0.15 g) from the furanmethanol (0.2 g) and A (0.1 g)

B.p. 130°–140°/$5\times10^{-2}$ mm Hg, oxalate salt m.p. 130°–133°.
Found: C,42.5; H,5.9; N,6.1; $C_{12}H_{22}N_2O_2S.2H_2C_2O_4.\frac{1}{2}H_2O$ requires: C,42.9; H,6.1; N,6.3%

(f)
2-[[4-Methyl-5-(1-pyrrolidinylmethyl)-2-furanylmethyl]thio]ethanamine (2.5 g) from the furanmethanol (3.9 g) and A (2.3 g)

B.p. 165°/0.06 mm Hg. UV. λmax (ethanol) 232 nm; 337 nm (ε9.450,460).

EXAMPLE B

5-[[2-(Amino)ethyl]thio]methyl-2-(dimethylaminomethyl)-3-furanmethanol

A solution of 5-[[2-(amino)ethyl]thio]methyl-2-(dimethylaminomethyl)-3-furancarboxylic acid, ethyl ester (0.75 g) in dry tetrahydrofuran (50 ml) at 0° was treated with a 0.5 molar solution of aluminium hydride in tetrahydrofuran (35 ml). After 2 hours water (6 ml) was added, and the filtered solution evaporated in vacuo. The oily residue was distilled affording the title compound (0.4 g), b.p. 170°/$10^{-1}$ mm Hg.

The oxalate salt was formed in and recrystallised from ethanol, m.p. 140°–142°.

Found: C,42.1; H,5.7; N,6.6; $C_{11}H_{20}N_2O_2S.2H_2C_2O_4$ requires: C,42.5; H,5.8; N,6.5%.

EXAMPLE C

5-[[2-(Amino)ethyl]thio]methyl-N,3-dimethyl-2-furanmethanamine (i)
3-Methyl-5-[[2-(1,3-dioxo-2H-isoindol-2-yl)ethyl]thio]methyl-2-furancarboxylic acid, methyl ester A mixture of 2-(thio)ethyl-1,3-dioxo-2H-indole (8.3 g) and sodium hydride (0.96 g) in dry dimethylformamide (100 ml) was stirred at 0° for 3 hours. A solution of 5-(chloromethyl)-3-methyl-2-furancarboxylic acid, methyl ester (8 g) in dry dimethylformamide was added and the mixture stirred for 18 hours.

The solvent was evaporated in vacuo and the residue was dissolved in diethyl ether (500 ml) and washed with water(500 ml). The ethereal extract was evaporated and the solid residue was crystallised from methanol yielding the title compound (11 g) m.p. 92°–93°.

Found: C, 60.4; H, 5.0; N, 4.1; $C_{18}H_{17}NO_5S$ requires: C, 60.2; H, 4.8; N, 3.9%.

(ii)
5-[[2-(Amino)ethyl]thio]methyl-N,3-dimethyl-2-furancarboxamide

Gaseous methylamine was passed into a solution of 3-methyl-5-[[2-(1,3-dioxo-2H-isoindol-2-yl)ethyl]thio]methyl-2-furancarboxylic acid, methyl ester (7.2 g) and sodium methoxide (0.08 g) in dry methanol (20 ml).

After 4 hours 2 M hydrochloric acid (100 ml) was added and the solution was extracted with diethyl ether (300 ml). The aqueous fraction was basified with 5 M sodium hydroxide (45 ml) and extracted with ethyl acetate (200 ml). The ethyl acetate extract was dried over anhydrous sodium sulphate and evaporation of the solvent gave the title compound (2.3 g) as a low melting solid.

UV λmax (ethanol) 264 nm (ε12,600).

Found: C,52.3; H,7.5; N,12.5; $C_{10}H_{16}N_2O_2S$ requires: C,52.6; H,7.1; N,12.3%.

(iii)

5-[[2-(Amino)ethyl]thio]methyl-N,3-dimethyl-2-furanmethanamine

A solution of 5-[[2-(amino)ethyl]thio]methyl-N,3-dimethyl-2-furancarboxamide (1.9 g) in dry tetrahydrofuran (20 ml) at 0° was reduced with a 0.5 molar solution of aluminium hydride in tetrahydrofuran (35 ml). After 4 hours boiling at reflux, water (9 ml) was added and the filtered solution was evaporated in vacuo. The residue was distilled affording the title compound (0.5 g) as a colourless oil, b.p. 110°/10$^{-1}$ mm Hg.

The oxalate salt was formed in ethanol and recrystallised from methanol/water, m.p. 198° dec.

Found: C,42.5; H,5.6; N,7.0; $C_{10}H_{18}N_2OS.2H_2C_2O_4$ requires: C,42.6; H,5.6; N,7.1%.

EXAMPLE D

5-[2-(Amino)propoxy]methyl-N,N,3-trimethyl-2-furanmethanamine

A mixture of 5-(dimethylaminomethyl)-4-methyl-2-furanmethanol (1.35 g) and potassium tert-butoxide (0.9 g) in dry dimethylformamide (3 ml) at 0° was treated with a solution of 2-chloropropylamine, hydrochloride (0.4 g) in dry dimethylformamide (2 ml). After 20 minutes at ambient temperature, the mixture was quenched with oxalic acid (2 g) and the solvent removed in vacuo. Excess anhydrous sodium carbonate was added and the product extracted into chloroform. The chloroform extract was purified by filtration and the solvent evaporated in vacuo. The residue was purified by column chromatography (silica, methanol: 0.88 ammonia 19:1) affording the title compound (0.1 g).

The oxalate salt was formed in and recrystallised from ethanol, m.p. 130°–131°.

Found: C,45.2; H,6.5; N,6.3; $C_{12}H_{22}N_2O_2S.2H_2O$ requires: C,45.3; H,6.7; N,6.6%.

EXAMPLE 1

(a)

N-[2-[[5-(Dimethylaminomethyl)-4-(1-methylmethyl)-2-furanylmethyl]thio]ethyl]-N'-methyl-2-nitro-1,1-ethenediamine A mixture of 5[[2-(amino)ethyl]thio]methyl-N,N-dimethyl-3-(1-methylethyl)-2-furanmethanmethanamine (1.0 g) and N-methyl-1-(methylthio)-2-nitroethenamine (0.6 g) in water (15 ml) was stirred at ambient temperature for 24 hours.

The solvent was removed in vacuo and the residue purified by column chromatography (silica/methanol) to give a white solid which was crystallised from methyl acetate and petroleumn ether (60°–80°) affording the title compound (0.9 g) m.p. 91°.

Found: C,53.6; H,8.1; N,15.6; $C_{16}H_{28}N_4O_3S$ requires: C,53.9, H,7.9; N,15.7%.

Similarly prepared from the corresponding diamines were:

(b)

N-[2-[[4-Bromo-5-(dimethylaminomethyl)-2-furanylmethyl]-thio]ethyl]-N'methyl-2-nitro-1,1-ethenediamine (0.55 g) from the diamine (0.6 g)

M.p. 64°–66°

Found: C,39.8; H,5.0; N,14.3; $C_{13}H_{21}BrN_4O_3S$ requires: C,39.7; H,5.3; N,14.3%.

(c)

N-[2-[[5-(Dimethylaminomethyl)-4-methoxymethyl-2-furanylmethyl]thio]ethyl]-N-methyl-2-nitro-1,1-ethenediamine (0.75 g) from the diamine (0.6 g)

m.p. 81°–82°

Found: C,49.9; N,7.4; N,15.5; $C_{15}H_{26}N_4O_4S$ requires: C,50.3; H,7.3; N,15.6%.

(d)

2-(Dimethylaminomethyl)-5-[[2-[[1-(methylamino)-2-nitroethenyl]amino]ethyl]thio]methyl-3-furanmethanol (0.3 g) from the diamine (0.4 g)

NMR. (CDCl$_3$) τ: −0.25 br m (1H); 3.4 s (1H); 3.9 s (1H), 4.2 br m (2H); 5.5 s (2H); 6.4 s (2H); 6.6 s (2H); 6.7 m (2H); 7.6–7.5 m (5H); 7.8 s (6H).

Found: C,48.7; H,7.2; N,16.0; $C_{14}H_{24}N_4O_4S$ requires: C,48.8; H,7.0; N,16.3%.

(e)

N-Methyl-N'-[2-[[4-methyl-5-(methylaminomethyl)-2-furanylmethyl]thio]ethyl]-2-nitro-1,1-ethenediamine (0.55 g) from the diamine (0.6 g)

UV λmax (ethanol) 235 nm, 329 nm (ε13,700, 17,650). λmin 283 nm.

Found: C,49.6; h,7.0; n,17.2; $C_{13}H_{22}N_4O_3S$ requires: C,49.6; H,7.0; N,17.8%.

NMR (CDCl$_3$) τ:−0.2 br s (1H); 2.7 brs (1H); 3.5 s (1H); 4.0 s (1H); 5.3 br s (1H); 6.1 s (2H); 6.6 m (2H); 6.9–7.4 m (5H); 7.5 s (3H); 8.0 s (3H).

(f)

N-Methyl-N'-[2-[[methyl-5-(1-pyrrolidinylmethyl)-2-furanylmethyl]thio]ethyl]-2-nitro-1,1-ethenediamine (0.5 g) from the diamine (0.75 g)

UV λmax (ethanol) 234 nm, 328 nm (ε14,700, 19,200) λmin 281 nm.

NMR (CDCl$_3$) τ: 0.75 br s (1H); 3.5 br s (1H); 3.45 s (1H); 3.99 s (1H); 6.3 s (2H); 6.46 s (2H); 6.75 br m (2H); 6.9–7.9 m (9H); 8.01 s (3H); 8.25 m (4H).

(g)

N-[3-[5-(Dimethylaminomethyl)-4-methyl-2-furanylmethoxy]propyl]-N'-methyl-2-nitro-1,1-ethenediamine hemihydrate (0.6 g) from the diamine (0.5 g)

UV λmax (ethanol) 229 nm, 327 nm (13,650, 18,300). λmin 278 nm.

Found: C, 53.6; H, 8.0; N, 16.5; $C_{15}H_{26}N_4O_4.\frac{1}{2}H_2O$ requires: C, 53.7; H, 8.1; N, 16.7%.

(h)

2-(Dimethylaminomethyl)-5-[[2-[[[1-(methylamino)-2-nitroethenyl]amino]thio]methyl]-3-furancarboxylic acid, ethyl ester (0.3 g) from the diamine (0.5 g)

UV λmax (ethanol) 224 nm (sh); 253 nm (sh); 329 nm (ε12,650, 9,600, 18,750).

TLC (silica/methanol: 0.88 ammonia 79:1) Rf 0.8.

EXAMPLE 2

N-[2-[[5-(Dimethylaminomethyl)-4-methyl-2-furanyl-methyl]thio]ethyl]-N'-methyl-2-nitro-1,1-ethenediamine A mixture of 5-[[2-(amino)-ethyl]thio]methyl-N,N,3-trimethyl-2-furanmethanamine (1.15 g) and N-methyl-1-(methylthio)-2-nitroethenamine (0.76 g) was heated in vacuo for 4 hours. The reaction mixture was purified by column chromatography (silica/methanol:0.88 ammonia 79:1) affording the title compound (0.45 g).

UV λmax 232.5 nm, 328 nm (ε14,800, 18,850), λmin 280 nm.

Analysis found: C, 50.0; H, 7.6; N, 16.5; $C_{14}H_{24}N_4O_3S.\frac{1}{2}H_2O$ requires: C, 49.8; H, 7.5; N, 16.6%.

EXAMPLE 3

(a)

N"-Cyano-N-[2-[[5-(dimethylaminomethyl)-4-methyl-2-furanylmethyl]thio]ethyl]-N'-methylguanidine Solutions of N-cyanoimidothiocarbonic acid, dimethyl ester (0.73 g) in ethanol (20 ml) and 5-[[2-(amino)ethyl]thio]methyl-N,N-3-trimethyl-2-furanmethanamine (1.15 g) in diethyl ether (15 ml) were mixed and after 18 hours a 30% solution of methylamine in ethanol (20 ml) was added. The solution was heated under reflux for 4 hours and the solvent was removed in vacuo. The residue was purified by column chromatography (silica/methanol: 0.88 ammonia 79:1) affording the title compound (0.6 g) m.p. 86°–88°.

UV λmax (ethanol) 224.5 nm (ε23,200).

Similarly prepared from the corresponding diamines were:

(b)

N"-Cyano-N-methyl-N'-[2-[[4-methyl-5-(1-pyrrolidinylmethyl)-2-furanylmethyl]thio]ethyl]guanidine (0.4 g) from the diamine (0.5 g)

UV λmax (ethanol) 225 nm (ε22,800).

NMR (CDCl₃) τ: 3.90 q (1H); 3.98 s (1H); 4.3 t (1H); 6.33 s (2H); 6.4 s (2H); 6.7 q (2H); 7.2 d (3H); 7.3 t (2H); 7.3–7.8 m (4H); 8.01 s (3H); 8.1–8.4 m (4H).

(c)

N"-Cyano-N-[2-[[5-(dimethylaminomethyl)-4-(1-methylethyl)-2-furanylmethyl]thio]ethyl]-N'-methyl guanidine (0.8 g) from the diamine (1 g)

m.p. 111°–112°.

Found: C, 57.0; H, 8.4; N, 21.0; $C_{16}H_{27}N_5OS$ requires: C, 57.0; H, 8.1; N, 20.8%.

EXAMPLE 4

N-[2-[[5-(Dimethylaminomethyl)-4-methyl-2-furanyl-methyl]thio]ethyl]-N'-nitroguanidine A solution of 5-[[2-(amino)ethyl]thio]methyl-N,N,3-trimethyl-2-furanmethanamine (1.14 g) and N-nitro-S-methyl-isothiourea (0.65 g) in ethanol (10 ml) was warmed for 5 minutes and stirred for 30 minutes at ambient temperature. The solvent was removed in vacuo and the residue purified by column chromatography (silica/methanol: 0.88 ammonia 100:1). The resulting oil was triturated with petroleum ether (40°–60°) and the solid residue crystallised from toluene yielding the title compound (0.5 g) as a white powder m.p. 84°–85°.

Found: C, 45.3; H, 7.0; N, 21.8; $C_{12}H_{21}N_5O_3S$ requires: C, 45.7; H, 6.7; N, 22.2%.

EXAMPLE 5

N-[2-[[5-(Dimethylaminomethyl)-4-methyl-2-furanyl-methyl]thio]ethyl]-N"-methanesulphonyl-N'-methylguanidine A mixture of 5-[[2-(amino)ethyl]thio]methyl-N,N,3-trimethyl-2-furanmethanamine (1.2 g) and N-methanesulphonyl-S,S'-dimethylimino-dithiocarbonate (1.3 g) in ethanol was heated under reflux for 3 hours. Methylamine (30% in ethanol: 10 ml) was added and the mixture left at room temperature overnight. The solvent was removed in vacuo and the residue purified by column chromatography (silica/methanol) affording the title compound (1.4 g) as an oil.

UV λmax (ethanol) 230 nm (ε10,250).

Found: C,46.0; H,7.3; N,15.1; $C_{14}H_{26}N_4O_3S$ requires: C,46.4; H,7.2; N,15.4%.

EXAMPLE 6

N-[2-[[5-(Dimethylaminomethyl)-4-methyl-2-furanyl-methyl]thio]ethyl]-N'-methylthiourea A solution of 5-[[2-(amino)ethyl]thio]methyl-N,N,3-trimethyl-2-furanmethanamine (0.5 g) and methylisothiocyanate (0.15 ml) in dry acetonitrile was stirred for 24 hours.

The solvent was removed in vacuo and the residue purified by column chromatography (silica/methanol) to yield the title compound (0.45 g) as a waxy oil.

UV λmax (ethanol) 212 nm, 239 nm (ε17,800, 20,750). λmin 221 nm.

Found: C,51.8; H,8.1; N,13.6; $C_{13}H_{23}N_3OS_2$ requires: C,51.8; H,7.7; N,14.0%.

EXAMPLE 7

N-Methyl-N'-[2-[[5-(methylaminomethyl)-4-phenyl-2-furanyl-methyl]thio]ethyl]-2-nitro-1,1-ethenediamine, hemihydrate (i) 5-(Chloromethyl)-3-phenyl-2-furancarboxylic acid, methyl ester A mixture of 3-phenyl-2-furancarboxylic acid, methyl ester (4 g), paraformaldehyde (0.87 g) and zinc chloride (0.74 g) in chloroform (5 ml) was treated with hydrogen chloride gas for 2½ hours. The mixture was poured onto saturated brine (100 ml) and extracted with chloroform (100 ml). The chloroform extracts were dried over sodium sulphate and the solvent evaporated in vacuo. The residue was distilled (Kugelrohr) affording the title compound (3.1 g) as an oil, b.p. 130°–140° C./10⁻¹ mmHg.

UV λmax (ethanol) 227 nm; 270 nm, (ε=18500; 12,500) λmin 247 nm.

(ii)

5-[[2-(1,3-dioxo-2H-isoindol-2-yl)ethyl]thio]methyl-3-phenyl-2-furancarboxylic acid, methyl ester A mixture of 2-(thio)ethyl-1,3-dioxo-2H-isoindole (2 g) and sodium hydride (0.24 g) in dry dimethylformamide (30 ml) was stirred at 0° for 2 hours. A solution of 5-(chloromethyl)-3-phenyl-2-furancarboxylic acid, methyl ester (2.5 g) in dry dimethylformamide was added and the mixture stirred for 18 hours. The solvent was evaporated in vacuo and the residue was dissolved in diethyl ether (150 ml) and washed with water (150 ml). The ethereal extract was evaporated and the solid residue was crystallized from methanol yielding the title compound (1.8 g) m.p. 108°–111°.

Found: C,65.5; H,4.5, N,3.3; $C_{23}H_{19}NO_5S$ requires: C,65.5; H,4.5; N,3.3%.

(iii)
5-[[2-(Amino)ethyl]thio]methyl-N-methyl-3-phenyl-2-furancarboxamide, hydrochloride Gaseous methylamine was passed into a solution of 5-[[2-(1,3-dioxo-2H-isoindol-2-yl)ethyl]thio]methyl-3-phenyl-2-furancarboxylic acid, methyl ester (4 g) and sodium methoxide (0.01 g) in dry methanol (50 ml). After 4 hours 2 M hydrochloric acid (100 ml) was added and the solution was extracted with diethyl ether (200 ml). The aqueous fraction was basified with 5 M sodium hydroxide (40 ml) and extracted with chloroform (200 ml). The chloroform extract was mixed with 2 M hydrochloric acid (100 ml) and the resulting solid was collected by filtration affording the title compound (1.6 g) as yellow needles. m.p. 189°–190°.

Found: C,55.1; H,6.0; N,8.7 $C_{15}H_{18}N_2O_2S.HCl$ requires: C,55.1; L H,5.9; N,8.6%.

(iv)
5-[[2-(Amino)ethyl]thio]methyl-N-methyl-3-phenyl-2-furanmethanamine

A solution of 5-[[2-(amino)ethyl]thio]methyl-N-methyl-3-phenyl-2-furancarboxamide (1.4 g) in dry tetrahydrofuran (100 ml) at 0° was mixed with a 0.5 molar solution of aluminium hydride in tetrahydrofuran (50 ml). After 6 hours boiling at reflux, water (6 ml) was added and the filtered solution was evaporated in vacuo. The residue was purified by column chromatography (silica/methanol) affording the title compound (0.45 g) as an oil, TLC (Silica/methanol: 0.88 ammonia 79:1) Rf 0.35.

NMR (CDCl$_3$) τ 2.6 m (5H), 3.6s (1H); 6.1s (2H); 6.2s (2H); 7.1m (2H); 7.3m (2H); 7.5s (3H); 8.5 br m (3H).

(v) N-Methyl-N'-[2-[[5-(methylaminomethyl)-4-phenyl 2furanylmethyl]thio]ethyl]-2-nitro-1,1-ethenediamine, hemihydrate A mixture of 5-[[2-(amino)ethyl]thio]methyl-N-methyl-3-phenyl-2-furanmethanamine (0.45 g) and N-methyl-1-(methylthio)-2-nitroethenamine (0.24 g) was stirred in water (5 ml) for 24 hours. The solvent was removed in vacuo and the residue purified by column chromatography (Silica/methanol) affording the title compound (0.3 g) as an amber glass.

NMR (CDCl$_3$) τ-0.3 br m (1H); 2.62s (5H); 3.4s (1H): 3.64s (1H); 3.5br s (1H); 6.2s (2H); 6.3s (2H); 6.75t (2H); 7.2m (5H); 7.6s (3H); 8.3 br m (1H).

Found: C,56.3; H,6.5; N,14.3; $C_{18}H_{24}N_4O_3S.\frac{1}{2}H_2O$ requires: C,56.1; H,6.5; N,14.5%.

EXAMPLE 8

Pharmaceutical Compositions

| (a) Oral Tablets 50 mg | for 10,000 tablets |
|---|---|
| Active ingredient | 500 g |
| Anhydrous lactose U.S.P. | 2.17 kg |
| Sta-Rx 1500 Starch* | 300 g |
| Magnesium Stearate B.P. | 30 g |

The drug is sieved through a 250 μm sieve and then the four powders are intimately mixed in a blender and compressed between 8.5 mm diameter punches in a tabletting machine.

(b) Injection for Intravenous administration (50 mg in 2 ml)

|  |  | % w/w |
|---|---|---|
| Active ingredient |  | 2.5 |
| Water for Injections BP | to | 100.0 |
| Dilute hydrochloric acid BP | to | pH 5.0 |

The active ingredient is dissolved with mixing in the Water for Injection, adding the acid slowly until the pH is 5.0. The solution is sparged with nitrogen and is then clarified by filtration through a membrane filter of pore size 1.35 μm. It is packed into 2 ml glass ampoules (2.2 ml in each) and each ampoule sealed under an atmosphere of nitrogen. The ampoules are sterilised in an autoclave at 121° for thirty minutes.

(c) Oral Sustained Release Tablets 150 mg

|  | for 10,000 tablets |
|---|---|
| Active ingredient | 1.50 kg |
| Cutina HR** | 0.40 kg |
| Anhydrous lactose U.S.P. | 2.060 kg |
| Magnesium Stearate BP | 40 g |

The active ingredient, anhydrous lactose and most of the Cutina HR are intimately mixed and then the mixture is moistened by mixing with a 10% solution of the remainder of the Cutina HR in Industrial Methylated Spirit OP 74. The moistened mass is granulated through a 1.2 mm aperture sieve and dried at 50° C. in a fluidised bed dryer. The granules are then passed through a 0.85 mm aperture sieve, blended with the magnesium stearate and compressed to a hardness of at least 10 kg (Schleuniger tester) on a tabletting machine with 12.5 mm diameter punches.

| (d) Oral Capsules 50 mg | for 10,000 capsules |
|---|---|
| Active ingredient | 500 g |
| Sta-Rx 1500* | 1700 g |
| Magnesium Stearate BP | 20 mg |

The drug is sieved through a 250 μm mesh sieve and is then blended with the other powders. The powder is filled into No. 3 size hard gelatin capsules on a suitable filling machine.

We claim:

1. Compounds of the general formula

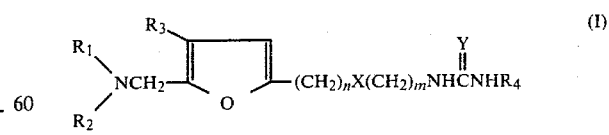

and physiologically acceptable salts and N-oxides, hydrates and biopreursors thereof, in which $R_1$ and $R_2$ which may be the same or different each represent hydrogen, $C_{1-8}$ alkyl, $C_{4-8}$ cycloalkyl, $C_{3-6}$ alkenyl, aralkyl with 1 to 4 carbon atoms in the alkyl residue or $C_{1-8}$ alkyl interrupted by an oxygen atom or a group $$-\underset{R_5}{\underset{|}{N}}-,$$

in which $R_5$ represents hydrogen or $C_{1-8}$ alkyl, or $R_1$ and $R_2$ may together with the nitrogen atom to which they are attached, form a saturated monocyclic 5 to 7 membered heterocyclic ring;

$R_3$ represents straight or branched chain $C_{1-8}$ alkyl, alkoxyalkyl with 1 to 8 carbon atoms in each alkyl residue, $C_{1-8}$ hydroxyalkyl, $C_{1-8}$ alkoxycarbonyl, alkyl thioalkyl with 1 to 8 carbon atoms in each alkyl residue, halogen or aryl;

$R_4$ represents hydrogen, $C_{1-8}$ alkyl, $C_{3-6}$ alkenyl or alkoxyalkyl with 1 to 8 carbon atoms in each alkyl residue;

X represents —O— or —S—;

Y represents =S, =O, =NR$_6$ or =CHNO$_2$ where $R_6$ represents hydrogen, nitro, cyano, $C_{1-8}$ alkyl, aryl, $C_{1-3}$ alkylsulphonyl or arylsulphonyl;

m represents an integer from 2 to 4 inclusive; and n represents an integer which is 1 or 2, or additionally when X is —S— n may also be zero.

2. Compounds as claimed in claim 1 of the general formula

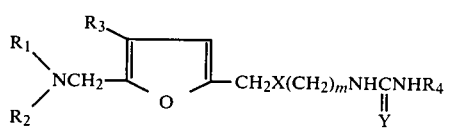

and physiologically acceptable salts, in which $R_1$ represents hydrogen or $C_{1-4}$ alkyl and $R_2$ represents $C_{1-4}$ alkyl or $R_1$ and $R_2$ together with the nitrogen atom form a pyrrolidine ring;

$R_3$ represents straight or branched chain $C_{1-4}$ alkyl, alkoxymethyl with 1 to 4 carbon atoms in the alkyl residue, hydroxymethyl, alkoxycarbonyl with 1 to 4 carbon atoms in the alkyl residue, phenyl or bromine;

X represents —S—, or —O—;

Y represents =S, =NR$_6$ or =CHNO$_2$ in which $R_6$ represents nitro, cyano or $C_{1-4}$ alkylsulphonyl;

$R_4$ represents hydrogen or $C_{1-4}$ alkyl; and m represents an integer which is 2 or 3.

3. Compounds as claimed in claim 1 which are:
N-[2-[[5-(dimethylaminomethyl)-4-methyl-2-furanylmethyl]thio]ethyl]-N'-methyl-2-nitro-1,1-ethenediamine;
N''-cyano-N-[2-[[5-(dimethylaminomethyl)-4-methyl-2-furanylmethyl]thio]ethyl]-N'-methylguanidine;
N-[2-[[5-(dimethylaminomethyl)-4-methyl-2-furanylmethyl]thio]ethyl]-N'-nitroguanidine;
N-[2-[[5-(dimethylaminomethyl)-4-methyl-2-furanylmethyl]thio]ethyl]-N'-methanesulphonyl-N'-methylguanidine;
N-methyl-N'-[2-[[4-methyl-5-(1-pyrrolidinylmethyl)-2furanylmethyl]thio]ethyl]-2-nitro-1,1-ethenediamine;
N-methyl-N'-[2-[[4-methyl-5-(methylaminomethyl)-2-furanylmethyl]thio]ethyl]-2-nitro-1,1-ethenediamine;
N-[2-[[5-(dimethylaminomethyl)-4-(1-methylethyl)-2-furanylmethyl]thio]ethyl]-N'-methyl-2-nitro-1,1-ethenediamine;
2-(dimethylaminomethyl)-5-[[2-[[1-(methylamino)-2-nitroethenyl]amino]ethyl]thio]methyl-3-furanmethanol;
N'-[2-[[4-bromo-5-(dimethylaminomethyl)-2-furanylmethyl]thio]ethyl]-N'-methyl-2-nitro-1,1-ethenediamine;
N-[2-[[5-(dimethylaminomethyl)-4-methoxymethyl-2-furanylmethyl]thio]ethyl]-N'-methyl-2-nitro-1,1-ethenediamine; and
N-[3-[5-(dimethylaminomethyl)-4-methyl-2-furanylmethoxy]propyl]-N'-methyl-2-nitro-1,1-ethenediamine.

4. Pharmaceutical compositions comprising a compound as defined in claim 1 together with at least one pharmaceutically acceptable carrier or diluent and optionally at least one other active ingredient.

5. A pharmaceutical composition as claimed in claim 4 in a form suitable for oral administration containing from 10 to 200 mg of the compound as defined in claim 1.

6. A method of treating a condition mediated through histamine H$_2$-receptors which comprises administering to a patient an effective amount of a compound as defined in claim 1 to relieve said condition.

* * * * *